US009167979B2

(12) United States Patent  
Skidmore et al.

(10) Patent No.: US 9,167,979 B2  
(45) Date of Patent: Oct. 27, 2015

(54) ATOMIC MAGNETOMETER SENSOR ARRAY MAGNETIC RESONANCE IMAGING SYSTEMS AND METHODS

(75) Inventors: Frank M. Skidmore, Gainesville, FL (US); Mark Davidson, Florahome, FL (US); Russell S. Donda, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 591 days.

(21) Appl. No.: 12/265,785

(22) Filed: Nov. 6, 2008

(65) Prior Publication Data

US 2009/0149736 A1  Jun. 11, 2009

Related U.S. Application Data

(63) Continuation-in-part of application No. PCT/US2008/004820, filed on Apr. 14, 2008.

(60) Provisional application No. 60/923,333, filed on Apr. 13, 2007, provisional application No. 60/966,099, filed on Aug. 24, 2007.

(51) Int. Cl.
*A61B 5/05* (2006.01)
*A61B 5/04* (2006.01)
(Continued)

(52) U.S. Cl.
CPC ........... *A61B 5/04009* (2013.01); *A61B 5/6814* (2013.01); *G01R 33/0354* (2013.01); *A61B 5/04008* (2013.01); *A61B 5/11* (2013.01); *A61B 2562/02* (2013.01); *A61B 2562/046* (2013.01)

(58) Field of Classification Search
CPC ............. A61B 5/04009; A61B 5/6814; A61B 5/04008; A61B 5/11; A61B 2562/02; A61B 2562/046; G01R 33/0354
See application file for complete search history.

(56) References Cited

U.S. PATENT DOCUMENTS 4,442,404 A * 4/1984 Bergmann .................... 324/309  
4,951,674 A    8/1990 Zanakis  
(Continued)

FOREIGN PATENT DOCUMENTS

WO    WO00/10454 A    3/2000  
WO    WO 0010454 A1 *  3/2000  
WO    WO 2005124380 A2 * 12/2005 ......... G01R 33/3415

OTHER PUBLICATIONS

Schwindt Peter et al Chip scale atomic magnetometer with improved sensitivity by use of the Mx technique. pp. 81102-081102 Applied Physics Letters, AIP, American Institute of Physics, Melville, NY vol. 90. No. 8 Feb. 21, 2007.

(Continued)

*Primary Examiner* — Bo J Peng  
(74) *Attorney, Agent, or Firm* — Timothy H. Van Dyke; Beusse, Wolter, Sanks & Maire, PLLC

(57) ABSTRACT

Devices disclosed according to various embodiments use one or more arrays of atomic magnetometers to directly detection of relaxation of magnetic field induced subatomic precession within a target specimen. The disclosed devices and methods relate to application of utilization of a magnetic sensor with unique properties requiring changes in design, allowing new functions, and requiring alternative analysis methodologies. Various embodiments are also directed to methods for obtaining and processing magnetic signals. These methods may take advantage of the unique spatial arrangement of the atomic magnetometers and the capacity sensors to be used in either a scalar or a vector mode. Various embodiments have advantages over current techniques utilized for imaging of anatomical and non-anatomical structures. Such advantages may include, for example: development of a wearable, portable array, lower power consumption, potential wafer-level fabrication, the potential for development of a more rapid signal, decreased need for development of strong magnetic fields, and lower cost allowing wider availability.

11 Claims, 14 Drawing Sheets

1a, 1B: Molded plastic cell including gas cell (1a) with embedded optics package (1b)  
2: Heater array  
3: VCSEL or fiber optic or other light source array  
4: Photodetector array One example of one potential design is shown for illustration; multiple variations on this theme are possible

(51) Int. Cl.
*A61B 5/00* (2006.01)
*G01R 33/035* (2006.01)
*A61B 5/11* (2006.01)

(56) References Cited

U.S. PATENT DOCUMENTS

| | | |
|---|---|---|
| 5,269,325 A | 12/1993 | Robinson et al. |
| 5,755,227 A | 5/1998 | Tomita et al. |
| 6,144,872 A | 11/2000 | Graetz |
| 6,195,576 B1 | 2/2001 | John |
| 6,370,414 B1 | 4/2002 | Robinson |
| 6,377,048 B1 * | 4/2002 | Golan et al. .................. 324/318 |
| 2002/0019589 A1 | 2/2002 | Tsukada |
| 2002/0169375 A1 * | 11/2002 | Nabetani ....................... 600/422 |
| 2004/0140799 A1 | 7/2004 | Romalis et al. |
| 2005/0052650 A1 | 3/2005 | Wu |
| 2005/0124848 A1 | 6/2005 | Holzner |
| 2005/0234329 A1 | 10/2005 | Kraus |
| 2006/0001423 A1 * | 1/2006 | Barbic .......................... 324/300 |
| 2006/0095220 A1 | 5/2006 | Vrba et al. |
| 2007/0167723 A1 * | 7/2007 | Park et al. ..................... 600/409 |

OTHER PUBLICATIONS

Groeger et al.: "Laser-pumped cesium magnetometers for high-resolution medical and fundamental research" Sensors and Actuators A, Elsevier Sequoia S. A. Lausanne, CH Vo. 129, No. 1-2, May 2006 pp. 1-5.

* cited by examiner

A  B  C  D 1a, 1B: Molded plastic cell including gas cell (1a) with embedded optics package (1b)
2: Heater array
3: VCSEL or fiber optic or other light source array
4: Photodetector array One example of one potential design is shown for illustration; multiple variations on this theme are possible

ATOMIC MAGNETOMETER SENSOR ARRAY MAGNETIC RESONANCE IMAGING SYSTEMS AND METHODS

RELATED APPLICATIONS

This application is a continuation-in-part of PCT/US08/004820 filed Apr. 14, 2008, which claims priority to U.S. Ser. No. 60/923,333, filed Apr. 13, 2007 and U.S. Ser. No. 60/966,099 filed Aug. 24, 2007, which are incorporated herein in their entireties.

FIELD

This relates to detection of relaxation of magnetic field induced subatomic precession within a target specimen, and can be applied in the fields of magnetic resonance imaging (MRI) and nuclear magnetic resonance spectroscopy (NMR).

BACKGROUND

Subatomic particles such as protons or neutrons, have the quantum property of spin. The overall spin of an atomic nucleus is dependant on the number of protons and neutrons in the isotope. Atomic nuclei with odd atomic numbers, such as hydrogen ($^1H$), have a net non-zero spin and therefore have a magnetic moment, while molecules with an even atomic number, such as Carbon-12 ($^{12}C$) have no net spin. When placed in an external magnetic field, polar molecules "precess" around an axis in the direction of the field. Subatomic particles align in either of two energy states: a low energy state or a high energy state. An external oscillating field will result in resonant aborption of energy by the subatomic particles. Resonant frequencies for particular molecules are directly proportional to the strength of the applied magnetic field, and are also related to the chemical composition of the molecule.

The property of magnetic spin is used in Nuclear Magnetic Resonance Spectroscopy and Magnetic Resonance Imaging to image target materials such as biological specimens, including human anatomic structures. In current, conventional Magnetic Resonance Imaging, a net polarization is developed by inducing a strong magnetic field. As noted above, subatomic particles within the nucleus of the atom align in either of two energy states, a high energy state or a low energy state. The alignment of the subatomic particles in these two energy states is responsible for the magnetic properties of target areas detected by magnetic resonance imaging and used to develop the image. The net magnetization vector has two components—a longitudinal component and a transverse component. The longitudinal component of the vector is related to an excess of aligned molecules (typically in biological molecules hydrogen atoms or protons) in the low energy state. The transverse component is due to the formation of coherence between the two subatomic energy states. Obtaining a magnetic resonance image includes two elements: an external magnetic field and a series of radio frequency pulses. In the case of biological specimens such as human anatomy, a radio frequency pulse of an appropriate energy level to excite protons within the specimen is applied to the specimen in the presence of an external magnetic field that ensures that only protons in a particular plane within the target are "on-resonance" and contribute to the signal. The radio wave disrupts processing molecules within the specimen. Recovery of longitudinal magnetization within the magnetic field after the radio pulse is discontinued is called the T1 relaxation of the specimen. Loss of phase coherence in the transverse plane is called the T2 relaxation. Both T1 and T2 relaxation result in electromagnetic waves in radio frequency wavelengths that can be detected by a receiving coil. Other properties of the signal can be detected using a variety of techniques with the external field, including using additional gradient magnetic fields, sending coils, and pick up coils to add information to the MRI image.

Conventional MRI has revolutionized medical care by providing crisp and useful internal images of human anatomy. However, conventional MRI has a number of disadvantages in the current state of the art.

1) First, conventional MRI can only image one slice of an anatomic specimen at a given time. Conventional MRI uses sending coils and receiving coils to generate repeated radio pulses through the specimen, with multiple signals read at one or a limited number of receiving coils. Multiple repeated signals with progressive signal averaging is needed to develop the image in each slice. Conventional MRI therefore requires significant time to obtain a useful image. The long time required to obtain an MRI image results in limitations in patient utility. For example, children, elderly adults, individuals with cognitive problems, and many other patient populations have difficulty staying within a conventional MRI magnet for the period of time needed to obtain optimal images.

2) Secondly, conventional MRIs require development of extremely large magnetic fields. Significant separation is required between MRI facilities and other facilities because of the significant magnetic effects on metal objects (such as surgical objects) and electronic equipment. The requirement of utilization of large magnetic fields prevents many patients, including individuals with metal prosthetic devices, individuals with shrapnel or bullet wounds, or individuals with pacemakers and deep brain stimulators, from obtaining MRIs.

3) Third, large, superconducting magnets are required to develop magnetic resonance images. Conventional MRIs are therefore bulky, and require dedicated rooms or suites. In some cases, large relatively lower quality mobile MRI devices are available that are transportable in trucks, however portability even in these devices is limited.

4) Finally, as can be understood from the above, conventional MRIs require a significant capital expense. The expense associated with installing and maintaining an MRI facility limits the use of this technology to typically hospital environments in first world countries.

The significant disadvantages of conventional MRI limit utility of that conventional technology. There is a need for a more portable, less cumbersome, and less expensive MRI scanning technology.

Recently, Clarke et. al. disclosed utilizing conventional SQUID based systems for detection of Nuclear Magnetic Spins (Clark et. al., U.S. Pat. No. 7,187,169). While disclosing a system that can detect low field NMR, and can be used for Magnetic Resonance Imaging, the system described by Clark et. al. is based on SQUIDs, which require cryogenic cooling. Further, SQUID systems are often bulky, expensive systems with limited capacity to allow for patient mobility.

Below, we describe a new atomic-magnetometer based, magnetic imaging technology, method and device. This subject technology can be more economical, portable and wearable. The technology we describe incorporates sensitive magnetic detectors that can function using significantly lower magnetic fields to develop signals. Our device is expected to result in lower cost to the consumer, and lower power consumption, potentially allowing the development of a device that can be used in an office practice, or more effectively in less advantaged countries. Further, our device is expected to use a lower magnetic field than conventional MRI scanners, opening the possibility of inter-operative magnetic imaging as well as imaging within an ambulance, on a commercial airliner or helicopter in the case of airborne emergencies or in a typical physician office environment.

This atomic-magnetometer based magnetic imaging system may be able to rapidly image the brain using an array of magnetic sensors.

The atomic-magnetometer based magnetic imaging system addresses sensor cross talk, shielding, mobility, and necessary algorithms for sensor calibration and data interpretation to allow development of a working magnetic imager using a new sensor type that reduces size and expense and increases portability.

For example, we now disclose, first that atomic magnetometers have several characteristics that may require new methodologies to deal with the issue of sensor cross-talk. Atomic magnetometers generate a magnetic field in the course of operation. This particular characteristic of these sensors may require special methodologies of operation and signal processing in order to produce a system that can actually measure MRI-like magnetic fields.

Secondly, many atomic magnetometers may detect magnetic fields along only very specific vectors. While potentially advantageous for source localization, this added directional capability requires specific data processing and design elements to allow development of a useful array for measuring MRI signals.

Third, the compact size of some atomic magnetometers, allows the development of an entirely new type of device and method. Specifically a mobile device and method allows the subject to freely move the head, neck, and in some cases allows ambulation while being continuously monitored. In some embodiments wearable magnetic imaging devices may be developed including wearable caps, helmets, blankets, or clothing like articles such as vests or wraps for arms, legs or torsos. A general term, "apparel," will be used in this description and in the claims to refer to items that are wearable while retaining general mobility. Apparel can include such caps, helmets, blankets or clothing described above, and also draperies, garments, wraps, casts, frames, structures, outerwear, gloves, shoes, masks, covers, suits, equipment or other items that can be or are designed to be worn by a human or other biological specimens while remaining relatively mobile. We use the phrase "specimen" to refer to portions of a person, a whole person, biological samples, or nonbiological samples. Further, in some embodiments, sheets of sensors may be used for imaging of biological or non-biological samples.

Fourth, some sensitive atomic magnetometers, such as SERF magnetometers, require provisions for magnetic shielding or field cancellation to be clinically useful. We enumerate a variety of devices and methods for these purposes.

Fifth, the possibility of utilizing large numbers of sensors allows the development of active sensor selection methods, which can in real time detect the optimal number and location of active sensors for a given clinical session or application.

Sixth, the atomic magnetometers operate at elevated temperature and thus may require some level of thermal isolation from the patient. This can come in the form of an insulating layer or active cooling.

Seventh, large numbers of atomic magnetometers can be arrayed around a body part of a subject or target specimen. Therefore, instead of developing information from the brain slice by slice using time average of multiple signals, induction of one or more RF signals may be utilized to generate a field in the specimen and precession, with multiple sensors capturing relaxation information from the entire specimen. This process will in some embodiments require much less time to obtain a useful image.

Eighth, the high sensitivity of some atomic magnetometers can require a smaller magnetic field, allowing in some cases a smaller magnetic generator and allowing the development of a portable, wearable imaging device. Therefore, atomic magnetometer based systems may allow the development of a low field MRI.

In this application, we describe various devices and methods that, in particular embodiments, serve the relevant clinical needs of mobility, ease of use, and lower cost. In various embodiments, atomic magnetometers, arrayed around a patient's head in a mobile helmet, provide the significant advantages of allowing more comfortable monitoring which is advantageous in many cases, particularly, for example in optimally measuring children and disabled patients. We describe a number of clinical utilizations made possible by a portable array. For example, we describe that the array proposed can, in addition to measuring NMR signals for the purposes of MRI, can also measure biologically generated signals. We also describe the components of a portable array in relation to signal processing, inter-sensor interference, and magnetic shielding.

SUMMARY

An improved method and apparatus for performing nuclear magnetic resonance (NMR) of a specimen can be obtained by first polarizing the nuclear spins in the specimen in a magnetic field and then detecting the nuclear magnetic resonance (NMR) signals from the specimen using at least one atomic magnetometer.

The atomic magnetometer can be a single atomic magnetometer device or an array of devices. The array may be arranged in an apparatus to accommodate any body part, such as a head covering. The atomic magnetometers can be supplemented with other sensors to detect other biologically generated magnetic fields.

The method and apparatus can be employed in way that allows the atomic magnetometer to be inserted into a specimen, such as a orifice of a biological target, to allow the magnetometer system to be proximate the specimen.

BRIEF DESCRIPTION OF THE DRAWINGS

Reference will now be made to the accompanying drawings, which are not necessarily drawn to scale, and wherein.

DESCRIPTION OF VARIOUS EMBODIMENTS

Various embodiments of the present invention will now be described more fully with reference to the accompanying drawings, in which some, but not all embodiments of the invention are shown. Indeed, this invention may be embodied in many different forms and should not be construed as limited to the embodiments set forth herein. Rather, these embodiments are provided so that this disclosure will satisfy applicable legal requirements. When the words "may," "can," "might" or the like are used, they mean that the associated feature or description is not a necessary, critical or required aspect of the broadest disclosed inventions, even though they may be desirable or preferred.

Overview of an Example Embodiment

We describe magnetic resonance imaging (MRI) systems that use Atomic Magnetometers to provide a wearable MRI with mobility, reduced size and cost. For optimal performance, various issues are addressed, including sensor crosstalk, electromagnetic shielding and cancellation requirements, and data registration and calibration. Since atomic magnetometers typically operate at a high temperature, in particular embodiments, in order to ensure patient comfort, the system comprises an array of atomic magnetometers and an insulating layer between the atomic magnetometers and the subject's head. The system may optionally also include magnetic shielding around at least some of the atomic magnetometers.

Figure 8:
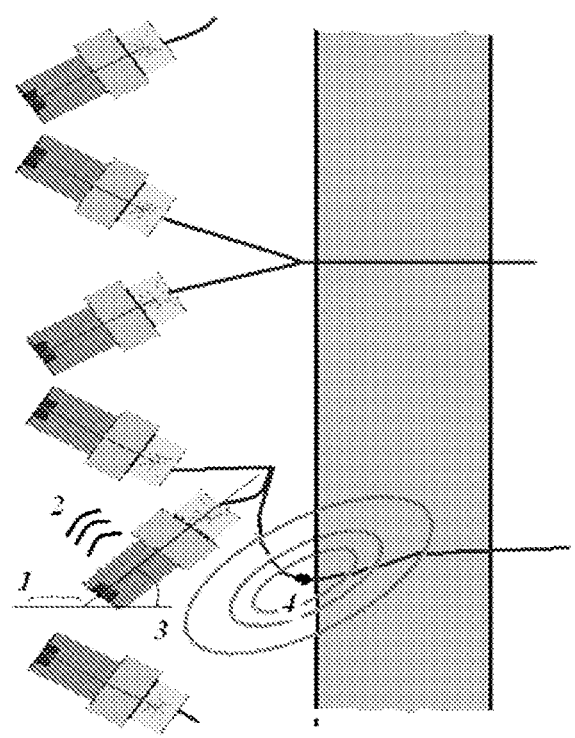
FIG. 8 shows the FIG. 7 parts assembled with portions broken away.

In a simple embodiment of this invention, nuclear spins are prepolarized in a low intensity magnetic field. Magnetic fields are then detected using atomic magnetometers. The computer then saves this information to memory. As part of this process, data will be processed by an algorithm that allows for imaging. Sensor registration techniques are utilized to optimize array output to maximize the overall accuracy of the array for the purposes of imaging. Optimally, the sensors will be calibrated and registered prior to use to allow sensor output to be accurately interpreted. The sensor registration process involves measuring a known combination of signals at a known position or multiple positions with respect to the sensor or sensor array and obtaining information from each sensor related to its position, direction, and response. Additionally, the sensor registration process characterizes cross-talk between sensors and noise in order to allow accurate signal deconvolution from interfering elements. Sensor registration is often important in accurate reading of large sensor arrays due to the many common sources of intra and inter-sensor differences in sensitivity, position, and interferences. Sensor registration, for example, may allow correction for inaccuracies in sensor placement, response, or operation as illustrated by FIG. 8. FIG. 8 shows example sources of error or aberrant signal that may occur within an atomic magnetometer array amenable to applied optimization. Four examples of aberrant signal are shown:

1. Sensor Offset Error in which an offset in sensors from other sensors in the array may result in alterations in sensor signal measurement.

2. Vibration Error in which sensors may move during the course of measurement related to nonrandom factors (for example patient head movement or internal mechanical vibration).

3. Angle Offset Error in which a fixed offset in sensor angle may cause a change in characteristics of a sensor signal measurement.

4. Unexpected internally generated magnetic noise in which an internal source of magnetic fields may occur and alter sensor signal measurement. The information obtained by, and transmitted from, the MRI can be used to estimate the magnitude, direction, and distance of the field generated by spin relaxation within the target area. Due to the vectoral information available in many atomic magnetometers, special algorithms are required to convert the raw data into useful information related to source localization.

More Detailed Discussion of an Example Embodiment

An MRI according to a particular embodiment comprises a helmet, a sensor array (e.g., an array of atomic magnetometers) disposed adjacent an interior surface of the helmet, and a heat insulator (e.g., a molded heat insulator) that is shaped to fit over the subject's scalp. The sensor array is disposed between the heat insulator and the helmet's interior surface.

The sensor array may, for example, include a plurality of atomic magnetometers that are arrayed adjacent the subject's scalp. Also, each sensor within a particular array of sensors may comprise a cluster of individual sensors that are adapted to cooperate to function as either a single scalar or directional magnetometer.

The atomic magnetometers can be chip-scale magnetometers, glass gas-cell magnetometers, or can consist of magnetometers constructed of gas cells molded from plastic cells that are either transparent to the light in the frequency of interest or have inset windows to allow the light to enter and exit.

A stacked array of two or more positioned atomic magnetometers with capacity to sense magnetic field vectors (see FIG. 1A) can be arrayed adjacent to a target. Sensors may also be arranged in such a way to allow scalar detection of field strength at a specific point in space. Alternatively, more complex arrangements may be utilized. It is understood that nearby sensors will generate magnetic fields during operation that will create an unwanted signal that will interfere with the capability of a given sensor to detect the target signal. In the case of an array of sensors, therefore, it is desirable to address inter-sensor cross-talk.

A number of strategies are disclosed to manage sensor cross-talk, including simple multiplexing, which is a strategy that can involve serially polling individual sensors. During polling, the sensor is typically operating and both detecting a field and generating a field. However, adjacent sensors may not be activated and, therefore, are neither generating a field nor detecting a field. Subsequently, activation of the first sensor is discontinued, and a second sensor is activated.

This method can prevent development of inter-sensor cross-talk. A potential disadvantage of this technique is that, in large arrays, the time to poll all sensors can be prohibitively long. A further refinement of this technique is serial polling of groups of sensors that do not experience cross talk. There are several parameters that are useful for selecting which sensor groups might be simultaneously activated. For example, in some atomic magnetometers, there can be certain angles of minimal sensitivity. Therefore, sensors with this property, when located at the appropriate angle, may be simultaneously activated with acceptably small inter-sensor interference. Once these sensors are activated, and make their measurement of the field, the sensors are de-activated.

Subsequently, another cluster of sensors with the same properties is activated, making their measurement. In this case, each cluster of sensors functions as a unit that can be safely activated with minimal inter-sensor interference, increasing the number of sensors that can be simultaneously activated during multiplexing. The distance between sensors, as well as relevant in-device shielding, can be used as one example way to determine which subgroups are selected for simultaneous activation.

Figure 6:
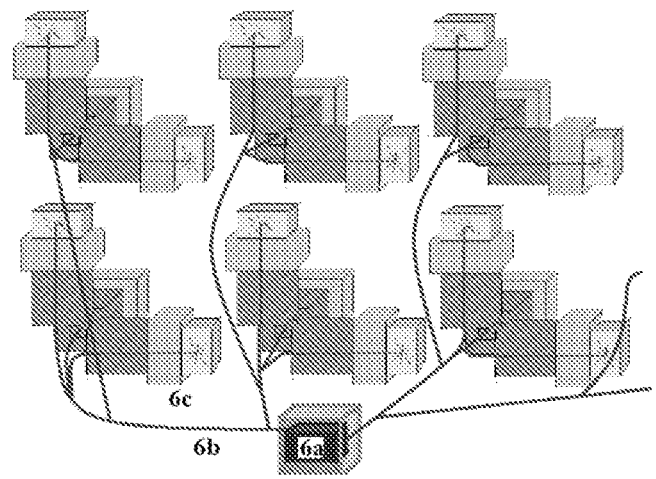
FIG. 6 is a schematic diagram showing how a single laser generator may be used to simultaneously illuminate multiple sensors.
Figure 7:
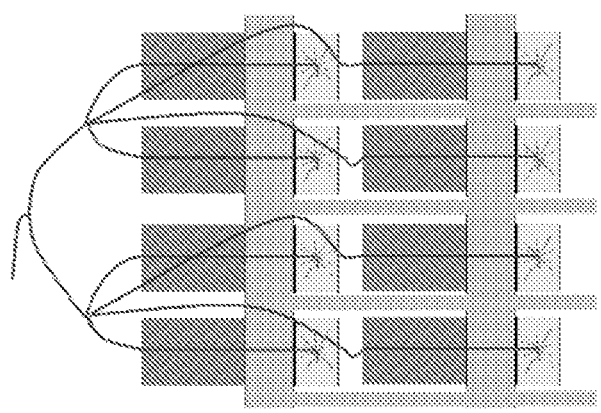
FIG. 7 is a schematic diagram showing how a single heat source may be used to simultaneously heat multiple sensors.

In some cases a single laser may be coupled to one or more cells using fiber optic cables (FIG. 6). In this schematic image, 6a represents a single laser source, 6b represents fiber optic coupling, and 6c represents a cluster of sensors. Similarly, collective heating of the array may be economical (FIG. 7).

Figure 9:
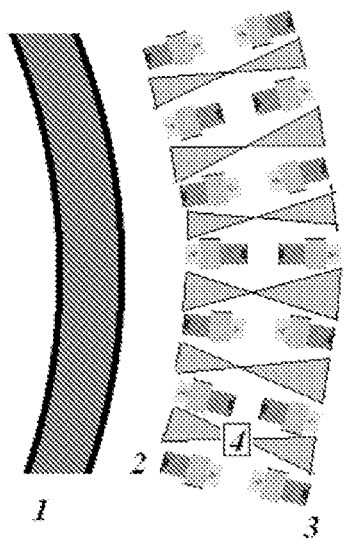
FIG. 9 is a schematic representation of shielding and positioning that may be utilized to minimize inter-sensor interactions.

FIG. 9 depicts shielding and positioning that may be utilized to minimize inter-sensor interactions. In FIG. 9, reference number "1" refers to insulation/internal structure; reference numbers "2" and "3" refer to alternating sensors; and reference number "4" refers to magnetic shielding.

Depending on the type of sensors utilized, sensors may generate spurious magnetic fields during operation, which may be measured by adjacent sensors. In an array, methods of packing the sensors may be required to mitigate these effects. In FIG. 9, the atomic magnetometer is assumed to generate a magnetic field related to the direction of light propagation within the sensor. In this case, alternating the direction of light propagation in the sensors, and/or placing sensors in a random orientation, may be utilized to minimize the generation of large scale field effects, although in this case local field effects might still apply. In the case of other atomic magnetometers, different angles may be utilized, such as positioning sensors at angles of low sensitivity, to minimize inter-sensor interactions.

Multiplexing may be utilized to periodically turn on and off sensors to allow temporal dissipation of magnetic field effects. In the case of atomic magnetometers, the speed of multiplexing can be limited by the relaxation time of the gas in the detection chamber. This relaxation time is typically on the order of microseconds, and is a function of gas composition, pressure, and temperature. Therefore, there is sufficient temporal resolution for applications such as functional imaging. Additionally, shielding may or may not be interposed between specific sensors or sensor pairs to direct magnetic field lines away from adjacent sensors. As a benefit, magnetic shielding (e.g., creating a window of measurability) may augment the direction sensitivity of a given sensor or sensors. Finally, signal processing may be utilized to remove known frequencies related to operation of sensors from measurements. It should be understood, in light of this disclosure, that many other configurations using these concepts are possible.

Signal processing algorithms can be utilized to allow localization and deconvolution of distal signals within a target by subtracting more proximal signals. Alternatively (or in addition), signal processing algorithms can be used to subtract environmental noise. Deconvolution may have the effect of reconstructing a three-dimensional map of the locations and intensities of the signals generated.

Because of the relatively small size of the sensors, a relatively high sensor density within a particular array of sensors may be utilized. For example, the sensors may be placed less than 3 mm from the subject's scalp in a closely packed array.

A second sensor (comprising a single magnetometer or cluster of magnetometers) may be positioned distal to a first sensor along the same axis (e.g., an axis that is perpendicular to the surface of the patient's head) at a sufficient distance to measure environmental noise. Because the first sensor is located closer to the signal source than the second sensor, subtracting the signals measured by the two devices will yield a difference in measured magnetic field. This information may then be used to determine signal and noise at the first sensor.

Figure 11:
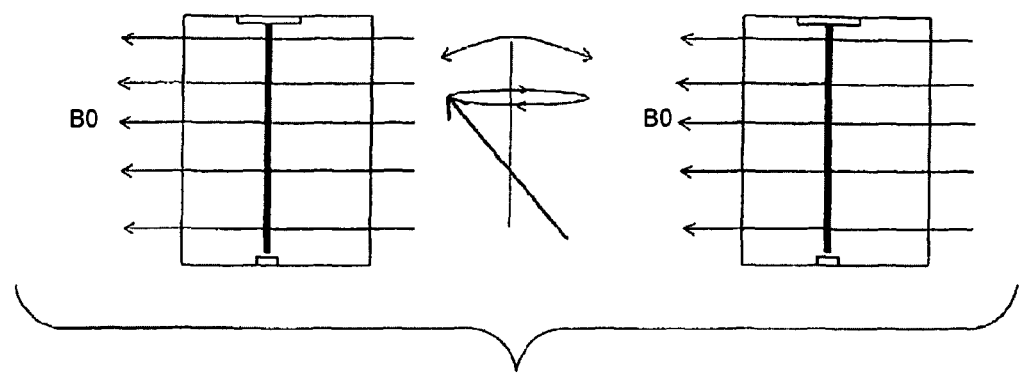
FIG. 11 is a schematic drawing showing the concept of utilizing one or more rotating magnetic dipoles to dynamically alter sensor detection characteristics.

Stacking and grouping of arrays of sensors or arrays of sensor clusters may be utilized to progressively screen signal from noise and to account for spatially uniform sources of noise, or other externally induced magnetic fields. Since atomic magnetometers or similar sensors develop magnetic fields in the course of normal operation (typically related to the direction of light propagation along the sensor), the direction of light propagation among sensors may be alternated, or a random pattern of orientation may be utilized (see FIG. 9) to minimize large scale field effects. In some cases, additional magnetic shielding (such as mu-metal shielding or active shielding) may be placed around a sensor or a cluster of sensors, for the purpose of further mitigating inter-sensor interference, and/or in order to provide a further screen for environmental noise. Since sensor-related magnetic fields typically have a particular magnitude and occur at a particular frequency, signal analysis techniques may be utilized to remove the influence of inter-sensor interference from the information derived from the sensors. While imaging can be performed using a prepulse and detection field, other additional features may be used to improve image quality. For example, Louis-Serge Bouchard, and Vasiliki Demas of Berkeley Labs (Patent Pending, University of California/Berkley, Patent ID pending) recently disclosed utilization of pairs of rotating fields through a sample to overcomes image distortions that typically occur when applying conventional NMR detection and MR imaging methods at low fields. We now disclose that in our device a number of methodologies can be used to improve imaging through dynamic alteration of sensor response. In this methodology, rather than introducing rotating fields through a specimen, field is altered at the sensor. Introduction of a small rotating magnetic field for example adjacent to one or more magnetometers can alter the detection profile of the magnetometer, selectively cancelling, masking, or enhancing magnetic fields coming from particular quadrants (FIG. 11). A rotating field may increase source information available from a given sensor, and may differentially affect adjacent magnetometers, leading to the potential for increased information for source localization from a sensor array, while avoiding the necessity for generation of fields over an entire specimen. In the figure in question, a precessing dipole is illustrated adjacent to two idealized magnetometers. A second induced field (B0) is also shown for the sake of illustration of the concept of interaction between a spinning field and a fixed field at the level of individual magnetometers; the direction of additional induced fields may be altered depending on the specific system requirements. In some cases, the strength or angle of rotation of the spinning dipole field may be altered dynamically.

Figure 12:
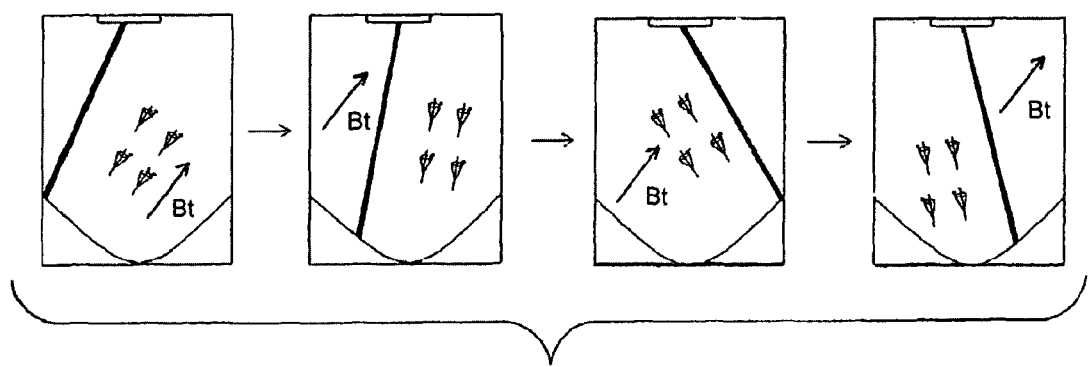
FIG. 12 is a schematic drawing showing the concept of utilizing alterations in laser direction to alter measurement characteristics of laser. Alteration of laser direction of a pump laser in a SERF or similar magnetometer is shown for illustrative purposes.

Similarly, altering the direction of the pump or probe laser may additionally allow increased information at the sensor for the purpose of source localization (FIG. 12). As in FIG. 11, the presence of an induced field is shown for informational purposes.

Figure 13:
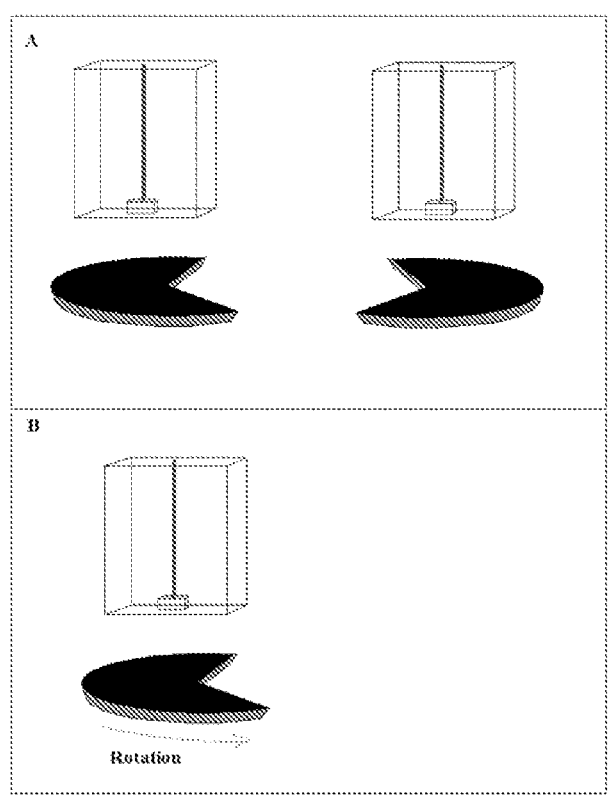
FIG. 13 is a schematic drawing showing partial shielding of sensors (13A, static partial shielding. 13B dynamic partial shielding).

In another example, magnetic shielding may be interposed between the detecting magnetometer and the specimen to constrain field detection (FIG. 13). Shielding may in some cases comprise a disk of mu-metal or other shielding material; other configurations are possible. In some cases, shielding may be rotated to alter directional sensitivity at a given sensor. Various other dynamic shielding strategies may also be used. While we disclose examples of methodologies to improve source localization in the specimen related to the SERF magnetometer, other atomic magnetometers with different detection profiles are available and the specific strategy utilized may depend on magnetometer characteristics.

Figure 14:
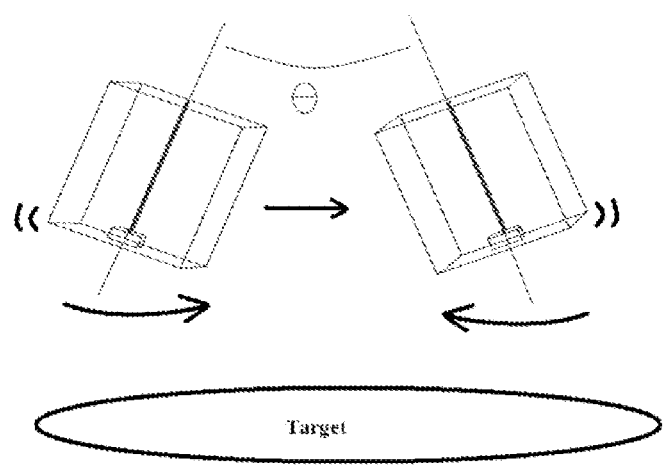
FIG. 14 is a schematic drawing showing dynamic alteration in sensor orientation.

In another example, sensor orientation may be altered to either improve targeting of a specific region or to allow dynamic alteration of vector sensitivity (FIG. 14). Various other possible strategies to alter sensor response exist. After reviewing this disclosure, therefore, various other alternatives for altering sensor response characteristics may occur to those skilled in the art.

Standard methods for detection and localization of target magnetic fields may be utilized to define regions of interest for further analysis. Fiducial markers may be used as necessary to define the relationship of sensors to the target.

Figure 1A:
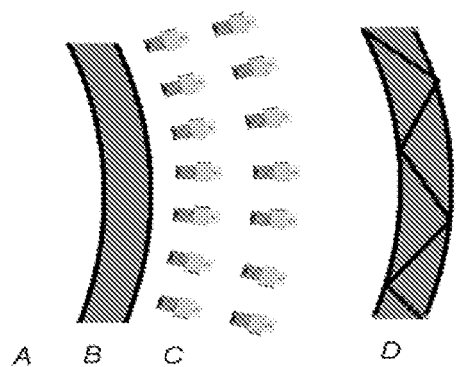
FIG. 1A is a cross-sectional schematic diagram of an exemplary MRI according to various embodiments.

Induction of a magnetic field in at least some of the various sensors within the MRI may allow these magnetometers to be used as specific, vector magnetometers. Examples of such specific, vector magnetometers are shown in FIGS. 1A-1G. FIG. 1A shows vector and gradient detection by a linear array in which A is the subject scalp, B is a heat insulator, C is an interior helmet space, and D is the external helmet array, which may include magnetic shielding such as Mu metal shielding. In this linear array, atomic magnetometers may be arrayed in a substantially linear formation substantially parallel to the subject's scalp. Additional atomic magnetometers one or more rows may be located substantially parallel to the row of atomic magnetometers closest to the scalp for improvement in targeting and noise reduction. Mathematical techniques across multiple sensors in the array may be used to derive directional information and distance.

Figure 1B:
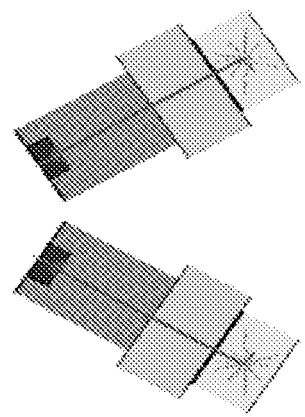
FIG. 1B is a plan view of two sensors that are paired for scalar detection in a plane.

FIG. 1B shows scalar detection in a bimodal array, in which 2 sensors may be paired to allow for scalar detection in a plane. In this design, some directional information is available as well, which may be combined with directional information from other sensors.

Figure 1C:
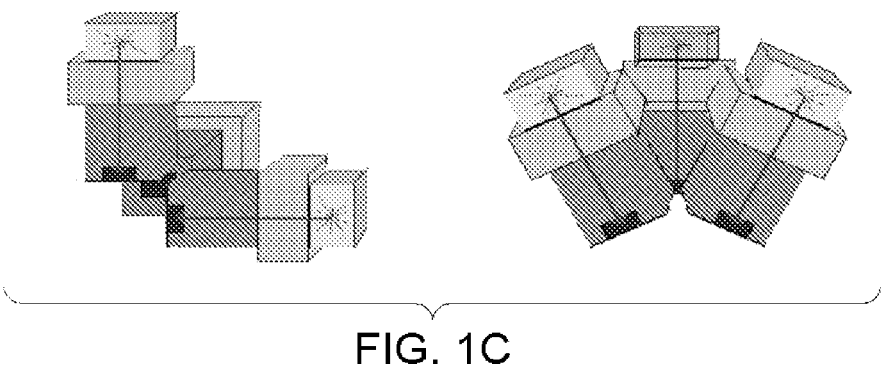
FIG. 1C is a perspective view of three sensors that are clustered and that are adapted to cooperate to act as a single scalar and vector sensor.

FIG. 1C shows vector and scalar detection in a cluster array, in which atomic magnetometers may be arrayed in clusters of 3 or more sensors at an appropriate angle. Two examples are shown to indicate that a variety of angles dependant on the direction of maximal sensitivity of the sensor may be used. In this setting, mathematical techniques may be used to operate the sensors to determine both the size and vector of the field.

Figure 1D:
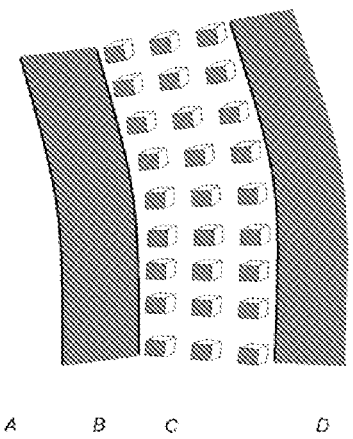
FIG. 1D is a cross-sectional schematic diagram of a portion of an exemplary MEG according to a particular embodiment.

FIG. 1D shows vector scalar and gradient detection in clusters of sensors (each cube may represent one or more individual magnetometers that collectively operate as a single sensor) that may be arrayed in groupings to maximize scalar, vector, and gradient detection of field. In this schematic, 3-detector clusters (shown as cubes) are arrayed in successive linear arrays. Levels A through D are arranged as in FIG. 1A.

Figure 1E:
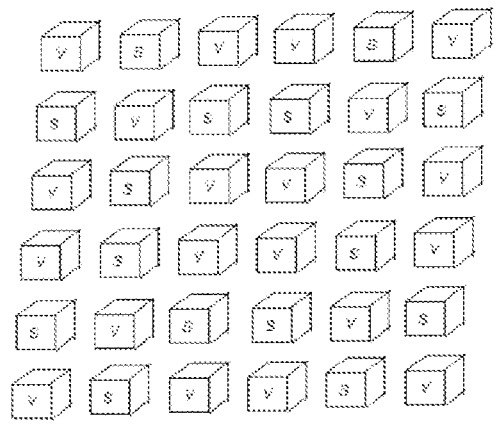
FIG. 1E is a schematic diagram depicting a single mixed layer of sensors that are, respectively, adapted to operate in vector and scalar modes.

FIG. 1E shows mixed arrays in which sensors may be grouped so that sensors in a vector mode ("V") are located adjacent to sensors operating in a scalar mode ("S"), and/or in overlapping arrays. One layer is shown, for the sake of simplicity, but multiple layers, with columns of vector and scalar sensors or overlapping vector and scalar sensors, may be used. The ideal arrangement of sensors is defined by the best mathematical fit for a particular application.

Figure 1F:
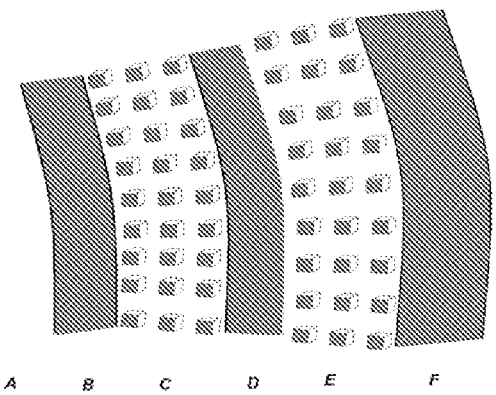
FIG. 1F is a cross-sectional schematic diagram of a portion of an exemplary MEG according to a particular embodiment that features an additional layer of sensors for noise reduction purposes.

FIG. 1F shows arrays with noise reduction in which an additional layer of sensors may be grouped outside of a shielded region to allow for noise reduction. In this schema, A is the scalp, B is insulation, C is a 3 dimensional vector, scalar, and gradient detection array (as described above), D is magnetic shielding, such as mu metal shielding, E is a noise reduction array, and F is a non-shielded outer shell. One or more arrays of sensors in vector, scalar, and/or gradient mode may be utilized, depending on the application.

Figure 1G:
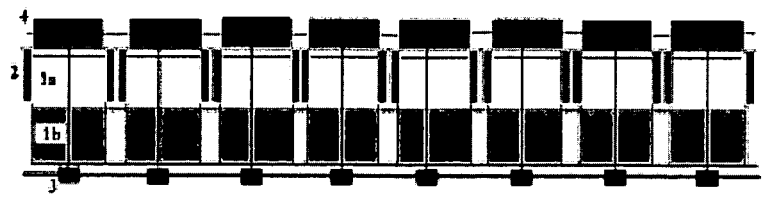
FIG. 1G is a schematic diagram depicting an array of sensors that are based on gas cells whose bodies have been molded from plastic.

FIG. 1G shows a plastic magnetometer array in which multiple sensors are fabricated using molded plastic cells. An anticipated device may include a molded plastic cell containing the gas cell (1a) and an embedded optics package (1b). A heater array (2), VCSEL or fiber optic or other light source array (3), and a photodetector array (4) may also be included.

Magnetic sensitivity may vary along the axis of the sensor, allowing clusters of sensors to mathematically calculate magnetic field direction. A plurality of groups of single or clustered sensors can be employed, preferably adapted to detect specific direction of magnetic field. With some types of sensors, the combination of two sensors (in which the two sensors are positioned relative to each other to form a predetermined angle) may be appropriate to create a scalar sensor. An example of such a combination of sensors is shown in FIG. 1B. This figure shows a bimodal array of sensors. In this figure, two sensors are paired to allow for scalar detection in a plane. In this design, some directional information may be available as well, which may be combined with directional information from other sensors. In the case of one exemplary device, three sensors arrayed at a non-zero angle detect both the magnitude and the direction of a magnetic field.

Three or more individual sensors may be arranged to form angles relative to each other (with each specific angle dependant on individual sensor properties) to allow for estimation of both field direction and gradient with respect to a single point—e.g., within a single cluster of sensors, as shown in FIG. 1C. In a cluster array, atomic magnetometers may be arrayed in clusters of one or more sensors at an appropriate angle. Two examples are shown to indicate that a variety of angles dependant on the direction of maximal sensitivity of the sensor may be used. In this setting, mathematical techniques may be used to operate the sensors to determine both the size and vector of the field.

The MRI may include two or more layers of sensors (See FIG. 1D). These layers of sensors may be used to gather field gradient information, which may be used to improve the spatial resolution of the field source. FIG. 1D shows clusters of sensors (each cube may represent one or more individual magnetometers that collectively operate as a single sensor) that may be arrayed in groupings to maximize scalar, vector, and gradient detection of field, allowing maximization of localization. In this figure, three-sensor clusters (shown as cubes) are arrayed in successive linear arrays. Levels A through D of FIG. 1D can be arranged as shown in FIG. 1A.

In various embodiments, the MRI's sensors may be alternatingly arranged within the MRI's various rows of sensors, as shown in FIG. 1E. In FIG. 1E, sensors may also be grouped so that sensors in a vector mode ("V") are located adjacent to sensors operating in a scalar mode ("S"), and/or in overlapping arrays. One layer is shown, for the sake of simplicity, but multiple layers, with columns of vector and scalar sensors or overlapping vector and scalar sensors, may be used. In most cases, the ideal arrangement of sensors is defined by the best mathematical fit for a particular application.

In addition, the MRI's sensors may be arranged so that magnetic shielding is positioned between a first array of sensors and another array of sensors, as shown in FIG. 1F. In FIG. 1F, an additional layer of sensors, with each sensor comprising one or more atomic magnetometers, is grouped outside of a shielded region to allow for noise reduction. In this figure: (1) item "A" is a patient's scalp; (2) item "B" is insulation; (3) item "C" is a three-dimensional vector, scalar, and gradient detection array; (4) item "D" is a layer of Magnetic shielding, such as mu metal shielding; (5) item "E" is a noise reduction array; and (6) item "F" is an outer shell. One or more arrays of sensors in vector, scalar, and/or gradient mode may be utilized, depending on the application.

Accordingly, the first sensor array may be utilized for signal detection, and the second sensor array may be utilized to assess the level of noise present in the signals measured by the first sensor array. More particularly, the signals measured by the first sensor array may include both magnetic fields from a target area within the patient's body (e.g., the patient's brain) and noise. However, because the second sensor array may be shielded from magnetic field's emanating from the target area, the second sensor may measure substantially only the noise adjacent the first magnetometer. Accordingly, the magnetic fields from the target area may be determined by subtracting the noise (as measured by the second array) from the signals measured by the first sensor array.

FIG. 1A depicts an example MRI according that may allow for vector and gradient detection. In this embodiment, the MRI includes: (1) an internal insulator that is adapted to insulate the subject's scalp from heat; (2) a sensor compartment that may optionally be thermally cooled; and (3) an outer shell that may comprise magnetic shielding (e.g., Mu metal shielding). The MRI can optionally include additional layers of sensors. These additional layers may be used, for example, as described above, for noise reduction purposes.

In FIG. 1A: (1) item "A" is a patient's scalp; (2) item "B" is a heat insulator; (3) item "C" is the interior of a helmet; and (4) item "D" is an external helmet array, which may comprise magnetic shielding such as Mu metal shielding. In a linear array, sensors are typically arrayed in a substantially linear formation substantially parallel to the subject's scalp. Additional sensors (one or more rows) may be located substantially parallel to the row of sensors closest to the scalp for improvement in targeting and noise reduction. Mathematical techniques across multiple sensors in the array may be used to derive directional information and distance.

As we will discuss again later with reference specifically to the figures, sensitivity of sensors across the axis of the sensor may also be dynamically altered using a variety of methodologies (see FIGS. 11-14).

Figure 2:
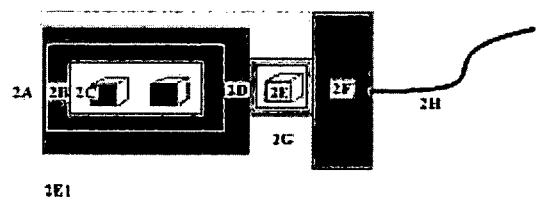
FIG. 2 is a cross-sectional schematic diagram of a sensor assembly according to a particular embodiment.

In the example of FIG. 2, a plurality of sensor assemblies may be individually placed adjacent to a target. For example, a plurality of sensor assemblies (such as the sensor assemblies shown in FIG. 2) may be attached directly to a subject's head using a suitable medical adhesive. Such assemblies may be used within a helmet, as well.

In FIG. 2: (1) item "2A" is a subject's scalp; (2) item "2B" is thermal insulation; and (3) item "2C" is a sensor array comprising one or more sensors. Each cube in this figure may represent one or more magnetometers grouped as a single sensor. Furthermore, in this figure: (1) item "2D" refers to magnetic shielding, including mu-metal shielding; (2) item "2E" refers to an unshielded sensor array; (3) item "2F" refers to external thermal shielding and electronics; (4) item "2G" refers to the body of the external device, and (5) item "2H" refers to a wire for transmitting information.

In FIG. 2, one sensor is shown by way of simplified illustration, but more than one sensor may be included in the array. The positions of the elements shown in this figure are also exemplary. Other positions, based on issues of best evaluating potential sources of noise, may be included. For example, sensors may be placed laterally adjacent the sensor (e.g., at location 2E1) or at other locations. Other mechanisms of transmitting information to a central processor (e.g. wireless communication) may also be used.

A plurality of sensors can be embedded into a helmet (e.g., adjacent the portion of the helmet that would be disposed immediately adjacent to the subject's forehead and/or temples when the helmet is worn by the subject). Such sensors may be used, for example, for screening purposes for noise reduction, or conversely to monitor eye movements (as described above) for a specific application.

Other focused groups of sensors can also be included. Also, focused arrays of sensors may be positioned, for example: (1) along the subject's spinal cord; and/or (2) over or around the torso or other anatomic regions. Such focused arrays may be used separately or in conjunction with cerebral sensors. Placement of sensors can, for example, depend on the region of interest from the perspective of imaging.

As noted above, sensors according to various embodiments may be vector sensitive. Vector-sensitive sensors that are most closely aligned with a particular focus may obtain a relatively weak signal or no signal if the field vector is aligned along an axis of minimal detection sensitivity. As the vector of the magnetic field aligns with more distant sensors, detection of the field depends on (1) the vector product of the field with respect to the vector of maximal detection of the sensor, and (2) the distance from the field source, as depicted in FIG. 3.

Figure 3:
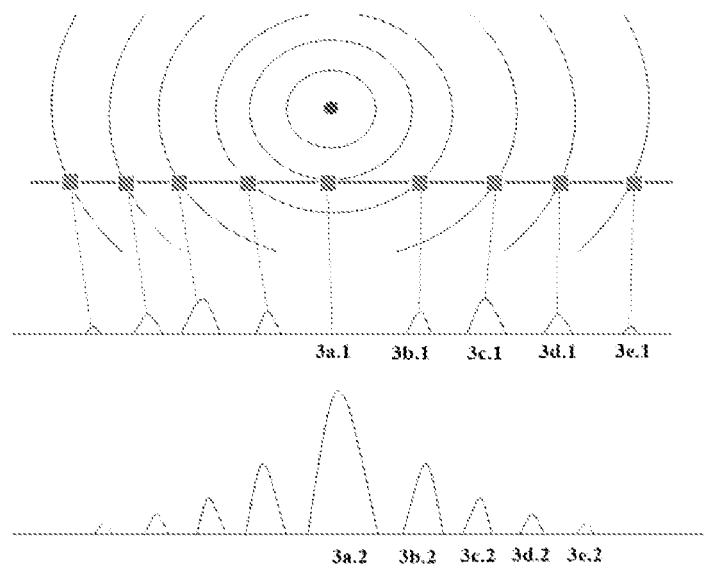
FIG. 3 depicts a magnetometer or group of magnetometers with sensitivity along a single field direction as compared to one or more magnetometers that have scalar sensitivity.

FIG. 3 demonstrates the concept of a vectoral and a scalar input. This figure shows a magnetometer or group of magnetometers with sensitivity along a single field line ($3a.1$ through $3e.1$) and magnetometers that have scalar sensitivity ($3a.2$ through $3e.2$). The magnetometers in FIG. 3 can be adapted for evaluating the location of a current traveling in a direction into the page. A schematic representation of magnetic field lines emanate from this current.

Turning further to FIG. 3, in locations $3a.1$ through $3e.1$, the sensors are displayed as being sensitive to field strength along the vertical axis. In this mode, even though field strength is high at location $3a.1$, effective detected strength in a vertical direction is 0. In arrays where three scalar sensors are arrayed at an angle, addition and subtraction of the relevant current strengths at each sensor can be used to develop information at each sensor in each mode.

In locations 3a.2 through 3e.2, the sensors are operating in a scalar mode. As the magnetic field decays by the inverse square of the distance, progressively smaller amounts of flux may be detected with increased distance. A single line of sensors is shown in FIG. 3, but the same or another sensor or group of sensors in a scalar or additive mode may be able to further define the absolute direction and magnitude of the current source.

If a multi-sensor array is utilized, a particular mathematical computation will, in particular embodiments, allow a scalar mapping of field strength. As each sensor has a unique response to the generated field, mathematical techniques can then be utilized to develop an image. Although not shown, the different angle of detection will also result in a change in shape of the detected signal which can also be used to better characterize the localization of the focus. A second row or more rows of sensors (not shown in FIG. 3) can be also used.

A row of sensors having vector and scalar detection capabilities can be arrayed in layers in order to determine information on dipole sources. These layers of sensors can be embedded in or adjacent a portable, helmet-shaped device (which is preferably of a weight that is suitable to be carried on the subject's head for an extended period of time while the subject is walking from place to place, or at least mobile). The layers of sensors can be arrayed within an internal layer of insulation and an external layer of shielding, with or without external noise reduction sensors.

Coils can be used to generate magnetic fields through a specimen. A magnetic field is generated when current is introduced into the coil that permeates the specimen. The introduction of a magnetic field through the specimen causes the magnetic dipoles to align and the spins to align. The field can then be discontinued. The sensors can then be activated, detecting the relaxation of the magnetic dipoles. A single or serial pulses may be utilized.

Multiple, magnetic coils may be oriented at orthogonal or other angles to generate fields through the specimen at a variety of angles. A radio-frequency (RF) coil may be utilized to generate a radiofrequency pulse through the specimen. Coils may be configured to generate a magnetic field gradient.

Figure 4:
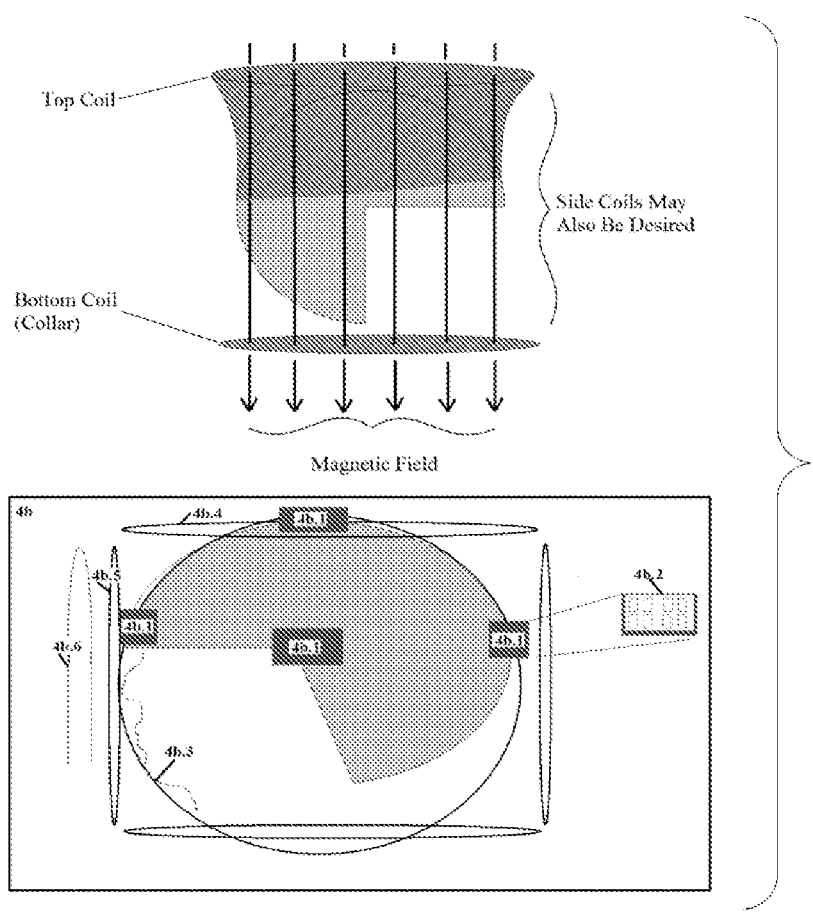
FIG. 4 is a schematic diagram of MRI devices according to particular embodiments.

Much like conventional MRI, those skilled in the art will recognize that there are myriad techniques for aligning and exciting nuclear spins. Appropriate analogs of these techniques adapted for this utilization are anticipated. The relaxation and localization of the resulting excitation is the subject of various embodiments. An exemplary embodiment of a portable MRI device is shown in FIG. 4. This embodiment includes an array of sensors located within the helmet. As discussed above, other localized arrays of sensors (such as the eyeglasses or paraspinal arrays, wraps, or form fitting devices) may be used simultaneously in conjunction with the helmet. Also as is discussed above, a variety of configurations of coils at various angles may be utilized. Also as is discussed above, coils may be configured to generate a magnetic field gradient, a polarizing field, or to deliver an RF pulse which may allow for example T2 contrast. The MRI device may be connected to a data analysis pack via an electrical cable, a fiber-optic cable, a wireless communication device, or other communication device. A microprocessor with data analysis software and a graphics display station may be included. A portable data analysis unit comprising the items above (recording input but with or without a remote graphics display capability) that can be attached to the subject may also be utilized. In a second exemplary embodiment, a magnetic field is produced by coils mounted on a bed, stretcher or another device which may or may not be mobile. Various possible sensing arrays may be utilized, including a flexible form fitting cap in lieu of a helmet. FIG. 4b shows another possible embodiment of a portable helmet as an example. In this example, atomic magnetometer arrays (4b.1) containing one or more sensors (4b.2) are placed around the head in combination with magnetic polarization coils at various orientations (4b.3-5) with an rf pulse generator (4b.6). While concentrated placement of sensors in several locations is shown, a diverse and continuous array is also possible. The number of coils, rf generators, number of sensors, and sensor placement will depend on the specific application.

The MRI's various sensor arrays may be adapted to communicate (in any suitable manner) with a data analysis pack. For example, in particular embodiments, the sensor arrays may be connected to communicate with the data analysis pack via an electrical cable, a fiber-optic cable, a wireless communication device, or other communication device.

A suitable data analysis pack may include, for example, suitable analysis tools, such as a photodiode, an A/D Converter, an Amplifier, High and Low Pass Filters, and/or a 50 and/or 60 Hz multiple notch filter. The data analysis pack may further include data analysis software and a graphics display station.

In applications where the MRI device is intended to be more mobile, the MRI can include a plurality of arrayed sensors that are connected to a portable power source and recording system. The MRI can be adapted to transfer (e.g., upload) data to a remote computer where the data may be processed and viewed. A rigid helmet may be used, or the sensors may be embedded in a flexible material that can be expanded to fit a larger head or can contract to closely fit smaller heads. Thus, the device can be flexible, or can come in different device sizes for different populations (e.g. pediatric versus adult), or both.

A portable device can also be used in a CT, PET, SPECT, or MEG scanner or other imaging scanner, allowing for MRI to be performed either temporally close to or, in the presence of appropriate time-locked field information, simultaneously with imaging or mapping using alternative techniques. Additionally, CT, SPECT, PET scanning, EEG, or MEG may be performed in temporal proximity to a MRI. In some embodiments, an ultrasound may assist with targeting a mobile array or be performed simultaneously or in close temporal proximity to add relevant information.

The sensor array may be configured to allow measurement of both MRI signals and signals generated by a biological specimen. For example, MRI may be combined in a device capable of also performing magnetoencephalography (MEG), magnetocardiography (MCG), or may measure other biologically relevant signals from structures such as peripheral nerves, spinal cord, or other tissues that generate biologically relevant magnetic fields. In these specific embodiments, the embodiments may be achieved either through reconfiguration of the existing sensor array according to specific requirements (e.g. MRI vs. MEG or MCG, for example), or utilization of one or more specialized sensor arrays designed for each purpose. The combination of MRI imaging with detection of signals generated from a biological specimen may allow more efficient co-registration of biologically generated signals with structural imaging.

An MRI device can be employed in environments that more closely approach a target within a specimen. For example, in specific embodiments a sensor array may be configured to be inserted through an orifice in a biological target. Such orifices may include the rectum, vagina, the mouth, or may include orifices that are created surgically.

Figure 10:
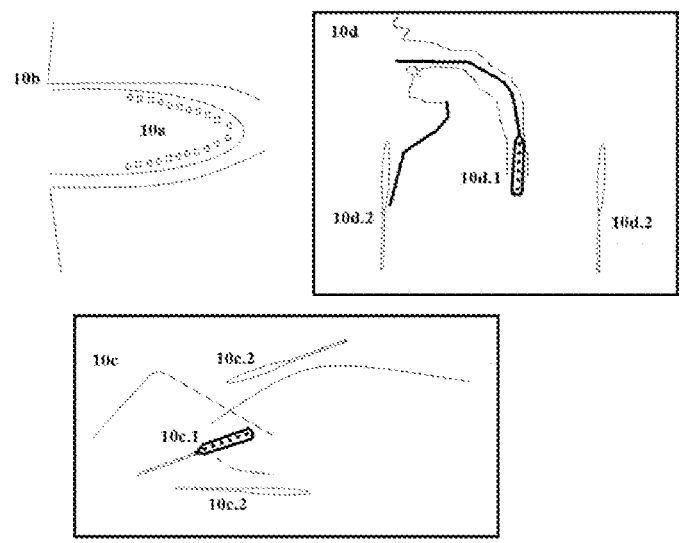
FIG. 10 is a stylized schematic of a sensor array configured to be inserted through an orifice in a biological target.

FIG. 10 shows a stylized schematic of an example of this concept. In FIG. 10, one or more atomic magnetometers are arrayed in a protective covering (10a) allowing insertion into the orifice (10b). Insertion of the sensor may be for the purpose of more closely approaching a biological target in which both combined imaging and sensing of a biological signal may be performed. In some cases, external coils to deliver magnetic field gradients may be provided. For example, vaginal insertion may be performed for the purposes of imaging a fetus and providing a fetal magnetoencephalogram or magnetocardiogram (10c, with 10c.1 representing the sensor, and 10c.2 representing external coils which may be desired). In another embodiment, a device may be inserted into the mouth for imaging of cortical or brainstem structures along with detecting relevant biologically generated signals from these structures. In another embodiment, insertion into the esophagus may allow imaging of the heart along with providing a magnetocardiogram (see 10d, with 10d.1 representing the inserted device, and 10d.2 representing external coils which may be desired). In this last example, the magnetocardiogram may allow better detection of atrial rhythms while additionally allowing development of images for co-registration. In other examples, imaging alone may be desired. For example, sensors may be inserted into the anus for the purpose of imaging the prostate to detect prostate tumors, into the esophagus for evaluation of esophageal or lung masses, or sensors may be inserted into the mouth for the detection of pituitary or nasopharyngeal tumors. In some embodiments, utilization of low fields as denoted may allow more effective development of T1 contrast. This may allow additionally imaging characteristics in the case of, for example, detecting tumors. A surgical approach may be desired in some cases for more effective approximation of the sensor array to the target structure. Utilization of an RF pulse may allow additional information such as T2 contrast. Those skilled in the art will note myriad other potential uses for inserted sensor arrays.

In some cases, it may be desirable to dynamically alter the sensor response, as described above. In some cases, dynamically altering sensor response may alter sensitivity, and therefore use of this technique depends on specific system requirements. FIGS. 11-13 describe examples of methods that may be utilized to dynamically alter the sensor response.

FIG. 11 shows placement of a dipole adjacent to one or more sensors. Dipole placement will depend on the system requirements, and therefore location of the dipole in this image is for illustrative purposes only. Additionally, we show a dipole for illustrative purposes however other methods of developing fluctuating magnetic fields at individual sensors may be used.

FIG. 12 shows alteration of laser direction to alter directional sensitivity of the sensor. Several positions are shown in the context of a continuously moving laser. Other configurations, including use of several static lasers in a single magnetometer, may also be utilized. In the figure, Bt represents a magnetic field from a target. The capacity of the magnetometer to measure the target field Bt is dependant on the direction of the pump laser with respect to the axis of Bt. As can be seen, in this regime altering direction of the pump laser alters the relationship between the target field Bt and the spin alignment defined by the pump laser.

FIG. 13 shows partial shielding of sensors from the signal source. FIG. 13A shows static shielding in the form of discs comprised of a shielding material such as mu metal or ferrite shielding. Different orientations are in this example used with different sensors. FIG. 13B shows a rotating disc. In this case, disc rotation can result in the development of magnetic fields, and use of this technique, including determination of appropriate time for disc rotation (e.g. continuously or during interstimulus and measurement intervals) will depend on system requirements.

FIG. 14 shows an example of altering the sensor orientation. Sensor orientation is altered manually in current practice during measurement, for example of cardiac sources; in this case however we disclose altering sensor response at discrete premeasured angles or rates in combination with appropriate software analysis techniques to improve the capacity of individual sensors to distinguish distinct sources within a specimen. Dynamically altering sensor angle may result in additional noise, and therefore altering sensor angles may be performed during measurement or during periods when measurement is not occurring depending on the specific system requirements desired.

The sensor array may be configured to continuously perform magnetic resonance imaging during mobile behavior, such as during ambulation, in order to provide a continuous functional magnetic resonance image. A portable MRI helmet may be combined with a portable MEG to allow, for example, first the development of an MRI image and then continuous MEG measurement. After reviewing this disclosure, various other alternatives may occur to those skilled in the art, such as combining a mobile MRI sensor array with MCG or other biologically generated signals.

The presence of multiple sensors may allow a more rapid measurement of external field-derived alterations in the magnetic moment within the target specimen, allowing for an image to be developed in a shorter time frame than conventional magnetic resonance imaging.

A sensor array with a specific field bias may be arrayed to triangulate maximal sensitivity in the direction of deep structure such as the locus coeruleus, basal ganglia, the substantia nigra, or other brainstem or deep structures of interest. Mathematical algorithms may be used to screen out noise (in this case, other brain activity as well as external activity). This can be used for a registration signal that then allows for further refinement of signal localization and isolation of deep brain signals.

Mathematical algorithms may be used to detect the presence of certain magnetically susceptible elements within the brain. In particular, the sensors can be configured to detect the effects of various forms of iron within the brain.

It should be understood that a number of different embodiments of the sensory array may fall within the scope of the present disclosure, including sensory arrays that are lightweight and potentially utilizable in mobile capable settings. Utilization of arrays that have specific vectoral capacities and that are adapted to be rotated and focused on an area of interest may also be utilized to improve signal detection.

Although this disclosure focuses, to a large extent, on imaging, the apparatuses and techniques described herein may be used in a wide variety of other types of applications such as magnetic resonance spectroscopy, for example.

A cooling fan may be needed in some configurations since each atomic magnetometer may incorporate heaters which heat the detection cell. Heating methods that operate over multiple sensors may have a greater total heat load and may result in the need for insulation or cooling methods. Cooled water or another cooling substance may be circulated in an insulator between the subject and the heater in order to minimize unwanted heat transfer.

Mathematical Analysis of Data

Unlike traditional MRIs, in which a single or a small number of pickup coils is typically utilized, atomic magnetometer-based MRIs may include larger numbers or a more dense placement of sensors for primary sensing, and a similar number of sensors may be utilized, for example, external to Mu metal shielding in a helmet for noise reduction purposes. With this large number of data points, specialized signal processing methods are used to sort signal from noise and optimize the detection capacity of the MRI. Therefore, methods of optimization can be used to evaluate signals and remove non-random errors and biases.

For example, optimization may be utilized to manage sensor registration. In some sensor arrays, the accurate registration of sensors in the network can cause problems. A number of sources of error, including sensor calibration offset, platform flexure, sensor perspective offset, sensor internal clock errors, and coordinate transforms can all degrade the accuracy of a network of sensors. Sensor registration can be seen as the process of accounting for (e.g., removing) non-random errors, or biases, in the sensor data. Without properly accounting for the errors, the quality of the composite image can suffer. Recently, Hirsch, Panos, et al. (Hirsch, Panos, 2006) developed a rapid algorithm for solving the sensor registration problem using a novel continuous meta-heuristic. This algorithm assumes that not all data is seen by all sensors, and that the correspondence of data seen by different sensors is not known a-priori. One process for measurement of systems comprising large numbers of sensors can be sensor registration, which broadly refers to applying correction factors to sets of data measured by more than one sensor. Examples of how sensor registration may be used in various embodiments are described below:

A magnetic sensor may read a particular field at the location of the sensor. Other sensors sample values over the region. With a measurement system comprising a distributed array of sensors, the magnetic field characteristics (magnitude, direction, and estimated distance) may be mapped. Furthermore, more detailed characterization of the field characteristics may be acquired if multiple sensors overlap. The field characteristics may be averaged over the readings from multiple sensors, for example. The process of aggregating data from multiple sensors is referred to as data fusion. Data fusion preferably employs sensor registration. In this example, magnetic field offsets among the various measurements (magnitude, direction, and estimated distance) are determined. Also, the relationship between the coordinates of a point measured relative to a specific sensor and the coordinates of the same point with respect to a different sensor can be determined. Furthermore, if the magnetic fields are measured as a function of time and time is read from a time stamp relative to an internal clock in each sensor, then synchronization of the clocks to a common reference is preferred. Further, although location of sensors within the array is presumed to be well known in most cases, and the probability of mis-identifying the location or orientation of a sensor is low, the probability is not zero as there may be errors in the fabrication device. FIG. 8 shows some examples of errors that might occur in a fabricated atomic magnetometer array. The figure is meant to be exemplary, and does not display all the types of errors that may occur in an array.

Turning to FIG. 8, an offset in sensors from other sensors in the array (see Item "1" in FIG. 8) may result in alterations sensor signal measurement. As shown in Item "2" of FIG. 8, sensor movement may be another source of errors. This may be caused, for example, when a sensor moves during the course of measurement (for example, due to patient head movement or internal mechanical vibration). In addition, a fixed offset in sensor angle may cause a change in characteristics of a sensor signal measurement (see Item 3 in FIG. 8). Furthermore, in some cases, an internal source of magnetic fields may occur and alter sensor signal measurement (see Item 4 in FIG. 8).

The chance of errors may increase as the size of the sensor array increases. In complex systems where multiple sets of data are collected from multiple signal sources by multiple sensors, sensor registration can be performed in each mode that will be used for data collection. For correct characterization of the signals, correct identification of the signals can be developed with a process to minimize local non-zero sources of noise (such as magnetic interference that might develop from a design flaw in magnetic shielding or insulation, improper sensor location registration, improper sensor orientation registration, or internal variability from sensor to sensor in sensitivity). One approach to sensor registration between two sensors involves minimizing a likelihood function associating the measurement of the signal by two or more sensors. With this approach, sensor registration falls into the category of optimization problems.

A method for registering a first magnetic sensor and a second sensor may be used using a two-step process wherein a systematic error function can be separated from an assignment function. The systematic error function can be based at least in part on a likelihood function associating a data element from the first set of measurements with a data element from a second set of measurements. The minimum of the systematic error function is generated to determine a correction factor for the systematic error. An assignment method is then used to assign a signal from a first plurality of signals to a signal from a second plurality of signals, based at least in part on the minimized systematic error function. Decomposing the problem into a systematic error problem followed by an assignment problems leads to a less complex, more computationally efficient method for sensor registration. In more specific embodiments, the systematic error function is minimized by applying a global minimization technique. An advantageous global minimization technique may be the Continuous Greedy Randomized Adaptive Search Procedure, which is computationally efficient and has a high probability of finding global minima, or a least a good estimate of global minima.

After the registration process (in the cases where it is used) is completed, data can be interpreted. The data coming from each sensor may be a convolution of signals from throughout a large area and the response function of the sensor. The result from these sensors is unintelligible without an algorithm for deconvolution of all of the responses of the sensors allowing for localization of each individual signal to a specific region of the brain. One example of a simple algorithm was mentioned earlier, in which common signals from adjacent sensors are subtracted to yield (to first order) signals from deep brain. A more complex algorithm allows for solution in 3 dimensions of the deconvolution of each sensor response. Without such an algorithm, the array of optical magnetometers may not yield a 3 dimensional image of the magnetic sources.

Other suitable methods of data optimization may also be utilized to optimize data from various embodiments of the MRI's sensor array. In addition, specific analysis techniques that are appropriate to specific sensor configurations may be developed.

Exemplary Suitable Sensors

As noted above, various embodiments can use optical atomic magnetometers to evaluate magnetic fields. In the current state of the art, many of these devices: (1) are small (e.g., less than 12 mm$^3$); (2) do not require cryogenic cooling; (3) are adapted to detect magnetic fields in the picoTesla or femtotesla range; (4) can be made to have a low power requirement (<200 mW and theoretically as low as 25 mW of power); and (5) can be designed to be produced using wafer-level fabrication techniques, potentially significantly lowering the cost of an MRI.

Further improvements in the state of the art are anticipated, and it should be understood that the techniques described herein may yield other designs for sensors with vector and scalar detection capacities on more compact scales or larger scales. The smaller overall potential scale raises the additional possibility that a more compact shielding array will be feasible. Larger scales may offer advantages of higher sensitivity or allow for more reliable operation.

Figure 5:
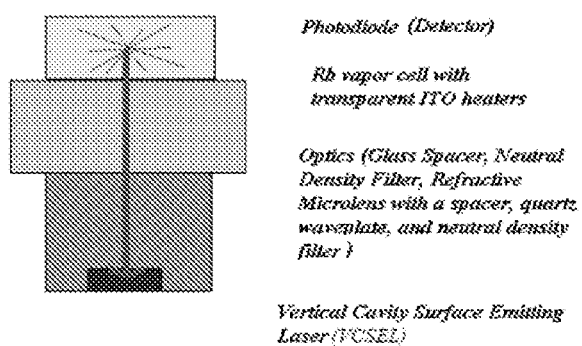
FIG. 5 is a schematic diagram of an exemplary atomic magnetometer that is suitable for use in various embodiments.

FIG. 5 shows an example of a particular style of chip-scale magnetometer. In this version, described by Moreland & Hollberg et. al. (2003), the VCSEL (laser) is tuned to the D1 line of $^{87}$Rb at 795 nm. A local oscillator modulates the current to the VCSEL at 3.4 GHz, half the hyperfine splitting of the Rb ground state, creating two laser sidebands that are resonant with two hyperfine ground states. The magnetic field is measured by probing the hyperfine transitions between two magnetically sensitive hyperfine states at optical frequencies. Another similar device from the same group uses a slightly different method, using a single beam Larmor frequency, which achieves maximal sensitivity to a field oriented at 45 degrees with respect to the sensor's optical axis (the device is not sensitive to magnetic fields perpendicular or parallel to the axis of the optical axis). With either device, arrangement of three sensors at a variety of angles will result in detection of a magnetic field in any direction, as well as determination of the vector and field strength of the field. FIG. 1G shows an exemplary design involving multiple sensors, in this case fabricated using molded plastic cells. In FIG. 1G, molded plastic cells are composed of a gas cell 1a with an embedded optics package 1b. A heater array 2 is disposed adjacent the molded plastic cell 1a/1b. A VCSEL, fiber optic array or other suitable light emitter provides a light source 3 at one end of the molded plastic cell. At the other end, a photodetector array is situated for detecting incident light.

Although the sensors of various embodiments are described herein as atomic magnetometers, it should be understood that any suitable sensor may be used in accordance with various alternative embodiments.

Use of a Single Laser Source for Multiple Sensors

While individual magnetometers may be provided with individual laser sources, in other embodiments a single laser (or multiple lasers) may be used to provide the light for a portion of a particular array of sensors, or even an entire array of sensors, as shown in FIG. 6. FIG. 6 is a representation of an example remote laser generator with fiber optic lines directing lasers to sensors for an atomic magnetometer array. In this Figure, item "6a" is a laser generator, item "6b" refers to fiber optic cables carrying lasers, and item "6c" refers to sensors. For vectoral sensors that utilize lasers, a single laser can be directed to multiple sensors. As can be seen in this representation, absolute orientation of the sensors is arbitrary and dependant on application. Although, in this schematic a limited number of sensors are powered, it is conceivable that a single laser might be utilized for a significant portion of the array, or the entire array.

Use of a Single Heating Source for Multiple Sensors

Similarly, instead of using individual heaters to heat the individual sensors (as is done in various embodiments), the MEG may include a uniform heating mechanism. This may be advantageous because individualized heaters often produce a magnetic field with the induction of electrical current that can interfere with the efficiency of the MRI's sensors, or require more complex multiplexing to avoid interference. Additionally, a method for uniformly heating sensors may result in a lower overall power requirement for a closely packed array of sensors. Suitable exemplary uniform heating mechanisms may include, for example, a heated gas or liquid either near or adjacent the array such as is shown in FIG. 7.

Turning to FIG. 7, a method to collectively heat an array of sensors (rather than have individual ITO heaters) may be employed. A number of possibilities exist, including the circulation of uniformly heated gas or transfer of heat along a uniformly heated liquid or solid that is adjacent to the array and that provides even heating throughout.

Multiplexing of Sensors

In the cases of some exemplary sensors, the operation of the sensor may cause magnetic effects that can be measured by other sensors. In this case, sequential temporal multiplexing of sensors may be utilized. In multiplexing, single or multiple sensors at various locations in the array can be triggered along a time course. Sensor registration techniques and optimization paradigms as described above may be utilized to account for magnetic effects (if multiple sensors are simultaneously triggered at a particular time), and temporal effects, allowing for signal reconstruction.

Magnetic Shielding

Atomic magnetometers may require magnetic shielding, such as shielding from external sources of noise. This may be accomplished in several ways. One way is to shield each individual sensor by one or more layers of one or more materials such as Mu metal or ferrites or aluminum which are capable of attenuating magnetic fields. Another way is to shield the entire array of atomic magnetometers by one or more layers of one or more materials such as Mu metal or ferrites or aluminum which are capable of attenuating magnetic fields. A third way is to surround each of the atomic magnetometers by coils which are actively driven to cancel out external noise fields. A fourth way is to surround the entire array of atomic magnetometers by a set of coils designed to be actively driven to cancel out external noise magnetic fields.

The shielding solutions can also be applied to the room or a sub-space within the room to allow a smaller field free region. This allows the magnetic shielding to be in place without the necessity of the additional weight and bulk attached to a helmet type device. In addition, combinations of all of these can be used to maximize the effectiveness of the shielding for a given size and weight limitation.

Shielding may be interposed between the signal source and the one or more sensors to improve the spatial resolution of the sensors. For example, the shielding may consist of a disk of mu metal or another high permeability material with a wedge shaped opening. The mu metal disk will interrupt incoming fields, thus limiting the signals detected, enhancing spatial resolution. Alternatively other shapes and materials may be used depending on the desired geometry of detection.

Conclusion

Many modifications and other embodiments of the invention will come to mind to one skilled in the art to which this invention pertains having the benefit of the teachings presented in the foregoing descriptions and the associated drawings. For example, as will be understood by one skilled in the relevant field in light of this disclosure, the invention may take form in a variety of different mechanical and/or operational configurations. Therefore, it is to be understood that the invention is not to be limited to the specific embodiments disclosed and that modifications and other embodiments are intended to be included within the scope of the appended exemplary inventive concepts. Although specific terms are employed herein, they are used in a generic and descriptive sense only and not for the purposes of limitation.

What is claimed is:

1. A portable, wearable apparatus for obtaining signals from a specimen, comprising:
   one or more magnetic field generators that apply an uniform polarizing magnetic field to polarize nuclear spins in a target anatomical region of the specimen such that a magnetic flux density of the applied magnetic field are uniform throughout the target anatomical region, wherein the one or more magnetic field generators are associated with an article of apparel such that they are portable together;
   an array of optical atomic magnetometers arranged on the article of apparel, wherein the array of optical atomic magnetometers comprises vector-mode atomic magnetometers, wherein each of the array of optical magnetometers comprises a container having a chamber filled with an atomic vapor, whereby the array of optical atomic magnetometers on the article of apparel detects magnetic field vector signals from a relaxation of polarized nuclear spins in the specimen when the applied magnetic field is removed; and
   one or more microprocessors for recording or processing the magnetic field vector signals to generate an anatomical map of the target anatomical region from the detected magnetic field vector signals.

2. The apparatus of claim 1, wherein the one or more magnetic field generators produce a millitesla field.

3. The apparatus of claim 1, wherein the one or more magnetic field generators produce a microtesla field.

4. The apparatus of claim 1, wherein the one or more magnetic field generator encodes a magnetic field gradient in the specimen.

5. The apparatus of claim 1, further including a radiofrequency generator to apply a radiofrequency pulse to the specimen.

6. The apparatus of claim 1, further including at least one sensor to measure biologically-generated magnetic signals.

7. The apparatus of claim 6, wherein at least one sensor measures a magnetoencephalogram.

8. The apparatus of claim 6, wherein at least one sensor measures a magnetocardiogram.

9. The apparatus of claim 6, wherein the sensor measures signals emanating from a spinal cord, peripheral nerve, muscle, or human fetus.

10. The apparatus of claim 1, further comprising at least one sensor and wherein a sensor response of the at least one sensor is dynamically altered.

11. The apparatus of claim 1, wherein the one or more magnetic field generators pulse a series of magnetic fields.

* * * * *